US009878122B2

(12) United States Patent
Mikheev et al.

(10) Patent No.: US 9,878,122 B2
(45) Date of Patent: Jan. 30, 2018

(54) NANO-AEROSOL GENERATION SYSTEM AND METHODS

(75) Inventors: Vladimir B. Mikheev, Dublin, OH (US); William C. Forsythe, Kennewick, WA (US); Benjamin N. Swita, Kennewick, WA (US)

(73) Assignee: Battelle Memorial Institute, Columbus, OH (US)

( * ) Notice: Subject to any disclaimer, the term of this patent is extended or adjusted under 35 U.S.C. 154(b) by 736 days.

(21) Appl. No.: 13/881,651

(22) PCT Filed: Oct. 25, 2011

(86) PCT No.: PCT/US2011/057767

§ 371 (c)(1), (2), (4) Date: Jul. 15, 2013

(87) PCT Pub. No.: WO2012/058246

PCT Pub. Date: May 3, 2012

(65) Prior Publication Data

US 2014/0041652 A1 Feb. 13, 2014

Related U.S. Application Data

(60) Provisional application No. 61/406,560, filed on Oct. 25, 2010, provisional application No. 61/471,195, filed on Apr. 4, 2011.

(51) Int. Cl.

*A61M 16/14* (2006.01)
*A61K 9/00* (2006.01)

(Continued)

(52) U.S. Cl.

CPC ........... *A61M 16/14* (2013.01); *A61K 9/0078* (2013.01); *A61K 9/14* (2013.01); *A61M 11/002* (2014.02);

(Continued)

(58) Field of Classification Search

CPC .. A61M 16/14; A61M 15/00; A61M 15/0086; A61M 16/12; A61M 2202/0208;

(Continued)

(56) References Cited

U.S. PATENT DOCUMENTS

| | | | |
|---|---|---|---|
| 5,616,165 | A | 4/1997 | Glicksman et al. |
| 8,029,595 | B2 | 10/2011 | Mukherjee et al. |

(Continued)

OTHER PUBLICATIONS

Wang et al., Aerodynamic Focusing of Nanoparticles: I. Guidelines for Designing Aerodynamic Lenses for Nanoparticles, Aerosol Science and Technology, 39:611-623, 2005.*

(Continued)

*Primary Examiner* — Todd J Scherbel
*Assistant Examiner* — Elliot S Ruddie
(74) *Attorney, Agent, or Firm* — Frank Rosenberg; C. Michael Gegenheimer

(57) ABSTRACT

The invention provides methods and apparatus for stable generation and delivery of solid nano-particles in aerosols that simultaneously maintain high nano-particle concentration, and which avoid coagulation and agglomeration of the nano-particles. The apparatus includes a Collison nebulizer is in communication with a plenum. The Collison nebulizer includes a port for introducing a helium gas flow into the Collison nebulizer. The plenum includes component(s) for providing flow of uniform axially symmetrical dry air around the nano-particles entrained in the helium gas flow in the plenum. Preferably, the plenum includes an uniformity screen and a reduction in the plenum circumference downstream from the uniformity screen. In some preferred aspects, the invention provides methods of introducing nanoparticles into the lungs of test animals. The present invention allows more than 0.5 mass % of the nano-particles to be deposited in an animal's lungs.

17 Claims, 6 Drawing Sheets

(51) Int. Cl.

| | |
|---|---|
| ***A61M 11/06*** | (2006.01) |
| ***A61M 15/00*** | (2006.01) |
| ***A61M 16/12*** | (2006.01) |
| ***A61M 11/00*** | (2006.01) |
| ***A61K 9/51*** | (2006.01) |
| ***A61K 9/14*** | (2006.01) |

(52) U.S. Cl.
CPC ........... *A61M 11/003* (2014.02); *A61M 11/06* (2013.01); *A61M 15/00* (2013.01); *A61M 15/0086* (2013.01); *A61M 16/12* (2013.01); *A61K 9/5115* (2013.01); *A61M 2202/025* (2013.01); *A61M 2202/0208* (2013.01); *A61M 2202/064* (2013.01); *A61M 2205/0244* (2013.01)

(58) Field of Classification Search
CPC ...... A61M 2202/025; A61M 2202/064; A61M 2205/0244; A61M 11/003; A61M 11/06; C01P 2004/34; C01P 2004/64; C01G 49/00; C01G 49/00009; C01G 49/02; C01G 49/06; C01G 49/04; C01B 33/112; A61K 9/0078; A61K 9/14; A61K 9/5115
USPC ............. 128/200.11, 200.14, 206.11, 207.18
See application file for complete search history.

(56) References Cited

U.S. PATENT DOCUMENTS

2009/0108090 A1 4/2009 Cooper et al.
2009/0258244 A1* 10/2009 Becker .................. B82Y 30/00 428/570
2009/0317336 A1* 12/2009 Gupta .................... B82Y 30/00 424/43

OTHER PUBLICATIONS

Schmoll, Linda, et al. "Nanoparticle aerosol generation methods from bulk powders for inhalation exposure studies", Nanotoxicology, Dec. 2009; 3(4); 265-275.

Martin, Andrew et al., "MRI Measurement of Regional Lung Deposition in Mice Exposed Nose-Only to Nebulized Superparamagnetic Iron Oxide Nanoparticles", Journal of Aerosol Medicine and Pulmonary Drug Delivery, 2008, 21(4); 335-341.

Costa, Daniel L. et al., "Comparative Pulmonary Toxicological Assessment of Oil Combustion Particles Following Inhalation or Instillation of Exposure", Toxicological Sciences, 91(1), 237-246(2006).

International Search Report from International Application No. PCT/US2011/057767 dated Feb. 7, 2012.

Written Opinion from International Application No. PCT/US2011/057767 dated Feb. 7, 2012.

International Preliminary Examination Report on Patentability from International Application No. PCT/US2011/05767 dated Apr. 30, 2013.

* cited by examiner

NANO-AEROSOL GENERATION SYSTEM AND METHODS

RELATED APPLICATIONS

This application is a national stage filing and claims the priority benefit of PCT/US2011/057767 filed Oct. 25, 2011 and also claims priority to U.S. Provisional Patent Application Nos. 61/406,560, filed Oct. 25, 2010, entitled NANO-AEROSOL GENERATION SYSTEMS and 61/471,195 filed Apr. 4, 2011.

TECHNICAL FIELD

This invention relates to methods and apparatus for the generation of gas streams containing solid nano-particles, and the high efficiency introduction of those particles into living organisms.

BACKGROUND OF THE INVENTION

Engineered nano-particles are defined as particles with diameter of less than 100 nm. A nano-aerosol is defined as a gas flow containing nano-particles. Workers that manufacture nano-particles, either deliberately or as a result of other industrial processes, are at risk from exposure to nano-particles via inhalation. Research studying the exposure of humans or animals to nano-particles by performing inhalation toxicity studies requires specially designed methods for the stable generation and delivery of nano-particles as nano-aerosols that simultaneously maintains high nano-particle concentration in the air, and which avoids coagulation and agglomeration of the nano-particles. Additionally, it may be beneficial to introduce certain materials as nano-particles as nano-aerosols to either animals or humans to treat disease or other harmful conditions. To date, no methods or apparatus have been shown to satisfactorily accomplish these objectives for wide range of compounds.

In a recently published paper (Schmoll, L. H. (2009). Nanotoxicology, 3(4): 265-275.) several known technologies were investigated to generate nano-aerosol out of commercially available nano-powder. The authors concluded that "none of the generation methods except for electrospray were able to produce an aerosol with a size distribution similar to that of the primary particle size indicated by the manufacturer, but most were capable of producing an agglomerate size distribution with a geometric mean <200 nm." The authors also noted that "electrospray was not able to produce a consistent concentration over time for all particles tested" (because of well known capillary clogging issues inherent for electrospray technology).

In the paper A R Martin, R B Thompson and W H Finlay, "*MRI Measurement of Regional Lung Deposition in Mice Exposed Nose-Only to Nebulized Superparamagnetic Iron Oxide Nanoparticles*" JOURNAL OF AEROSOL MEDICINE AND PULMONARY DRUG DELIVERY, Volume 21, Number 4, 2008, pp. 335-341, Finlay et al. describe the use of superparamagnetic iron oxide nanoparticles in magnetic targeting of inhaled aerosols to localized sites within the lung and as contrast agents in magnetic resonance imaging (MRI). In the experiments described in the paper, Finlay et al. examine the feasibility of measuring regional lung deposition of iron oxide nanoparticles using MRI. Mice were exposed nose-only to nebulized superparamagnetic iron oxide nanoparticles. The droplet size distribution in the inhalation chamber was measured using a time-of-flight device. Regional concentrations of iron in the left and right lung were assessed with MRI by measuring the longitudinal relaxation times (T1) of the lung tissue in exposed mice, compared to a baseline group. The total mass of iron that deposited in the lung of each exposed mouse was only 0.0006+/−0.0002% (mean+/−1 standard deviation, n+/−6) of the mass of iron introduced into the inhalation chamber. Based on these results, estimation shows that the delivery-deposition efficiency, measured as the [Total Deposited Mass]/[Total Inhaled Mass] of only 0.039%. Finlay et al. state that "This result is consistent with previous studies, in which nose-only, flow-by inhalation chambers have been shown to be extremely inefficient in terms of the amount of aerosol delivered to the lungs of rodents." citing Nadithe V, Rahamatalla M, Finlay W H, Mercer J R, and Samuel J: Evaluation of nose-only aerosol inhalation chamber and comparison of experimental results with mathematical simulation of aerosol deposition in mouse lungs. J Pharm Sci. 2003; 92:1066-1076 and Costa D L, Lehmann J R, Winsett D, Richards J, Ledbetter A D, and Dreher K L: Comparative pulmonary toxicological assessment of oil combustion particles following inhalation or instillation exposure. Toxicol Sci. 2006; 91:237-246. The inefficiency of introducing materials as an aerosol of few micron size into animals via nasal inhallation as described by Finlay and others is problematic because in many cases the materials that are to be tested or used via nasal inhalation are expensive and hard to manufacture.

Accordingly, there remains a need for methods and apparatus that provide stable generation and delivery of nano-particles of wide range of compounds in aerosols that simultaneously maintain high nano-particle concentration in the air, and which avoid coagulation and agglomeration of the nano-particles. There is a further need for methods and apparatus that provide stable generation and delivery of nano-particles of wide range of compounds in aerosols in a manner that improves the efficiency of introducing these nano-particles into animals through nasal inhalation of the nano-particles.

SUMMARY OF THE INVENTION

The present invention provide methods and apparatus for producing a highly concentrated flow of solid nano-particles. The present invention is superior to prior art methods because the present invention avoids the coagulation and agglomeration of nano-particles noted in prior art methods. As such, the present invention is capable of producing a highly concentrated flow of nano-particles having an average size of 100 nm or less, 50 nm or less, and 30 nm or less.

The apparatus of the present invention includes a Collison nebulizer in communication with a mixing-drying plenum. The Collison nebulizer includes a port for introducing a helium gas flow into the Collison nebulizer. Preferably, but not meant to be limiting, the helium gas flow is introduced into the Collison nebulizer at a pressure of 94 psi or more. The mixing-drying plenum may include a port for providing flow of dry air processed through a uniformity screen around the nano-particles entrained in the helium gas flow in the plenum. The plenum preferably has a reduction in the circumference at some distance from the uniformity screen.

The methods of the present invention preferably begin by synthesizing the nano-particles using conventional micro-emulsion method followed by preparation of nano-particles colloidal suspension in water. The nano-particles are then introduced into a Collison nebulizer as a colloidal suspension in water. Collison nebulizers have long been recognized as a technique for the efficient aerosolization of various liquids.

Typically, Collison nebulizers are operated with a flow of air in the presence of a liquid in a manner as described in May K. R. The Collison Nebulizer. Description, Performance & Application J. of Aerosol Science, Vol. 4, #3, p. 235 (1973) and Gussman, R. A. Note on the Particle Size Output of Collison Nebulizers, Am. Ind. Hyg. Assoc. J (45). (1984). As such, the operation and use of Collison nebulizers to generate aerosols from liquids is well understood by those having ordinary skill in the art, and no further description of Collison nebulizers is necessary to apprise those having ordinary skill in the art of the function and use of Collison nebulizers in the present invention.

In the present invention, in order to increase nano-aerosol concentration without increasing aerosol particle size (avoiding coagulation-agglomeration) helium gas is used in the Collison nebulizer instead of air, and, preferably, the helium flow into the Collison nebulizer is at a pressure of up to 94 psi (5.5 bar) or more. The nano-particles are thus entrained into the helium gas flow within the Collison nebulizer. The resultant nano-particles entrained in the helium gas flow are then directed out of the exit of the Collison nebulizer and into a plenum. At the entrance to the plenum, a flow of gas, while not meant to be limiting, preferably a mixture of dry air and oxygen, can be processed through a uniformity screen provided around the nano-particles entrained in the helium gas. At some distance from the uniformity screen, there is a reduction in the circumference of the plenum. This generates a venturi effect when the nano-particles entrained in the helium gas flow and surrounded by the flow of gas (preferably dry air and oxygen) reach the portion of the plenum with the reduced circumference, thereby accelerating and mixing the nano-particles entrained in the helium-air-oxygen gas flow. The resulting suspension of solid nano-particles can then be passed to an animal by providing a nose port, allowing an animal to breath the nano-particles through the nose port, and depositing the nano-particles provided as a colloidal suspension in water in the animal's lungs. Preferably, 0.5% of the nano-particles provided as a colloidal suspension in water are deposited in the animal's lungs. More preferably, 1.0% of the nano-particles provided as a colloidal suspension in water are deposited in the animal's lungs, and more preferably at least 1.5% of the nano-particles provided as a colloidal suspension in water are deposited in the animal's lungs.

While the method of the present invention can be used to generate an aerosol flow of a wide variety of particles, in one example the nano-particles comprise $SiO_2$. The present invention allows the formation of a stream containing entrained nano-particles having an average particle size of 100 nm or less. In one example, the present invention was shown to generate nano-particles having an average particle size of 50 nm or less. In another example, the present invention was shown to generate nano-particles having an average particle size of 30 nm or less (in some embodiments between 20 and 100 nm).

The present invention fills a need and is particularly useful in inhalation in-vivo studies wherein it is desirable to introduce high concentrations of nano-particles in a highly efficient manner to test the effects of the nasal inhalation of such nano-particles on living organisms.

Unless otherwise indicated, "%" nano-particles means mass %. As the term is used herein, "nano-particles" refers to solid nano-particles; it does not mean liquid nano-particles. The inventive nanoparticle aerosols are preferably highly concentrated; preferably having at least $1\times10^6$ particles, more preferably at least $2\times10^6$ particles, still more preferably at least $4\times10^6$ particles per cubic centimeter (cc); and in some embodiments in the range of $1\times10^6$ to $1\times10^8$ particles, in some embodiments in the range of $1\times10^6$ to $1\times10^7$ particles per cc. In other preferred embodiments, the inventive nano-particle aerosols comprise at least 10 mg nano-particles per cubic meter, more preferably at least 20 mg nano-particles per cubic meter.

"Average particle size" refers to the median number average particle size; in alternative embodiments, the invention may instead be characterized by mean number average, median or mean diameter size, or mass average particle size; and can be measured using standard equipment, preferably the equipment referred to herein; for example, an aerosol having an "average particle size" of less than 100 nm has a median (based on number) particle size of less than 100 nm, but in alternative embodiments, the invention could be characterized as having a mass average median particle size of less than 100 nm, and all such characterizations are intended to be included within various embodiments of the invention.

In this invention, "psi" refers to "psi gauge" or "psig" and bar also refers to gauge. Preferably, He enters the Collison nebulizer at a pressure of at least 80 psi (5.5 bar), preferably at least 94 psi (6.5 bar), in some embodiments in the range of 5.5 to 14 bar; more preferably in the range of 5.5 to 7 bar. The helium entering the Collison nebulizer preferably contains less than 10 mass % oxygen, and is preferably pure (100%) He.

Preferably, the dry air comprises a mixture of dry air with dry pure oxygen. For example, the dry air could comprise at least 30 mass % oxygen, in some embodiments between 25 and 50 mass % oxygen. Preferably, the dry air enters the plenum in a cross-flow direction (as shown by the inlet 6 in FIG. 1), and then made more axially uniform by passage through a uniformity screen. The uniformity screen does not filter out particles, but creates a partial barrier to flow such that a more uniform axial flow of dry air is formed. This axial flow surrounds the helium-entrained nano-particles as they flow into the plenum.

Preferably, the helium stream enters the plenum through a tube that passes through the uniformity screen. The outlet of the tube is preferably at least 5 cm (in some embodiments at least 10 cm) away from the downstream decrease in plenum diameter. The decrease is diameter is preferably at least a 1 cm decrease (in our examples, the diameter decreased from 3.5 cm to 2.2 cm); or, in terms of percentages, preferably at least a 10% decrease, more preferably at least 20% decrease in diameter, in some embodiments at least 30%. The tube 5 carrying the nano-particles entrained in helium is preferably at least 5 cm in length. The tube length after the decrease in diameter is preferably at least 10 cm, more preferably at least 20 cm or at least 50 cm, in some embodiments 10 to 100 cm. In this length, drying of the nano-particles occurs which may stabilize the nanoparticles and prevent or reduce agglomeration. The tube disposed after the decreased diameter section can be used to deliver the aerosol to a nose port, which could be disposed in a nose port carousel for dosing a plurality of (non-human) test animals. In some preferred embodiments, the test animals are mammals such as mice.

In some embodiments, the volumetric (i.e. molar) ratio of dry air to helium is in the range of 0.5 to 2, in some embodiments about 1:1. Since the helium stream and dry air are mixed in the plenum, the air mixture reaching the animal subject contains sufficient oxygen for normal respiration.

The scope of this invention should be evaluated with reference to the claims appended hereto. In reading the claims it is intended that when words such as “a”, “an”, “at least one”, and “comprising” are used there is no intention to limit the claims to only one item unless specifically stated to the contrary in the claims. In narrower embodiments, the invention can be characterized by replacing the broad term “comprising” with the narrower terms “consisting essentially of” or “consisting of.”

BRIEF DESCRIPTION OF THE DRAWINGS

The following detailed description of the embodiments of the invention will be more readily understood when taken in conjunction with the following drawings.

DETAILED DESCRIPTION OF THE PREFERRED EMBODIMENTS

Figure 1:
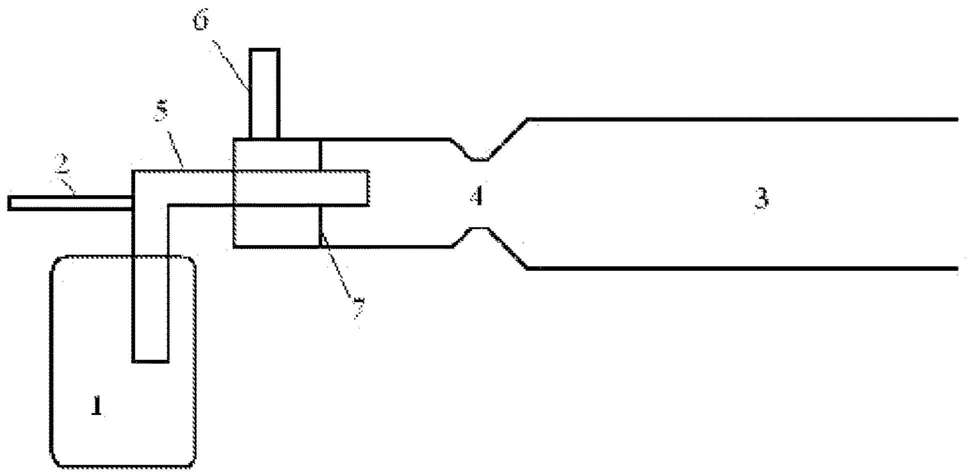
FIG. 1 is a schematic illustration of the apparatus of the present invention used in proof of principle experiments.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

To demonstrate an exemplary embodiment of the present invention, a series of experiments were conducted. The first of these experiments demonstrated the ability of the present invention to generate nano-size aerosol out of several types of nano-particles such as $SiO_2$ (15, 30, 50, 100 nm) and $Fe_3O_4$ (15 nm), and Fe3O4 (15 nm) with different surface modification [—COOH and —$N(CH_3)_3$] suspended in deionized water. Those having ordinary skill in the art and having the benefit of the examples set forth in this disclosure will recognize that the method of the present invention can be used with a multiplicity of nano-particles types, including any metal oxide, and including any metal oxide with surface modifications and functional groups attached.

A Collison nebulizer was coupled with a specially designed drying-dilution-mixing flow-chamber as shown in FIG. 1. As shown in FIG. 1, the device included a Collison nebulizer 1. The Collison nebulizer 1 was in communication via a tube 5 with plenum 3. The Collison nebulizer 1 included a port 2 for introducing a helium gas flow into the Collison nebulizer. The plenum 3 had a port 6 for providing flow of dry air processed through the uniformity screen 7 around the nanoparticles entrained in the helium gas flow in the plenum. The uniformity screen 7 was a stainless steel mesh, however any material permeable to a gas that would change a swirling flow to a symmetrical flow around the central flow of nanoparticles would suffice. At some distance from the uniformity screen, plenum 3 was configured with a reduction in the circumference 4.

Nano-particles were fabricated using the microemulsion method for nano-particle synthesis. Those having ordinary skill in the art will recognize that other conventional methods for generating nanoparticles in solution, such as a precipitation method, could also be used. These particles were then suspended in water colloidal solution and supplied to the CollisOn nebulizer. Aerosols generated by this device were analyzed using both an on-line Scanning Mobility Particle Sizer (SMPS, TSI) and an Electric Low Pressure Impactor (ELPI, DEKATI). Micro-Orifice Uniform-Deposit Impactor (MOUDI, MSP) data were taken and Scanning Electron Microscopy (SEM) analysis was also provided.

A wide range of aerosol generation conditions was investigated. Tests were performed using different carrier-gases at different pressure, dilution, system flow rates, relative humidity, and varying geometric configurations of the flow-mixing-dilution-drying system. Results were reproduced by repeating measurements during different days for several weeks. The nano-aerosol generation system was designed to be coupled with nose-only exposure carousel that may contain several tiers allowing dozens of nose-ports for inhalation experiments and simultaneous monitoring of exposure conditions. The results of these experiments demonstrated that nano-aerosols generated with 30, 50, and 100 nm $SiO_2$ nano-particles can be maintained close to the primary particle size avoiding coagulation and agglomeration. Measurements of aerosol size distribution at ~20 nm range (and below) interfered with water particles background. Stability of the nano-aerosol generation (without refreshing of liquid suspension) was confirmed for up to ~1 hour of continuous operation (for longer duration of exposure gradual slow increase of nano-particles concentration in the suspension due to water evaporation should be taken into account).

Further increase of the nano-particle concentration in the liquid suspension leads to the aerosol size increase (due to agglomeration), but still allowing operation within a reasonable nano-size range (below or close to 100 nm). Increasing of aerosol size close to 100 nm helps to increase aerosol mass concentration hence making total inhaled mass amount measurable using different methods of post exposure analysis. Proof of principle experiments as well as preliminary study on in-vivo nano-particles inhalation exposure followed by magnetic particle detection analysis were conducted. The results on nano-aerosol characterization are shown below.

TABLE 1

| 30 nm $SiO_2$ | Number Particle Size | Diameter Particle Size | Surface Particle Size | Volume Particle Size | Mass Particle Size |
|---|---|---|---|---|---|
| Median (nm) | 38.5 | 48.5 | 63.8 | 98 | 98 |
| Mean (nm) | 44 | 57.8 | 85.6 | 153.9 | 153.9 |

TABLE 1-continued

| 30 nm $SiO_2$ | Number Particle Size | Diameter Particle Size | Surface Particle Size | Volume Particle Size | Mass Particle Size |
|---|---|---|---|---|---|
| Geo. Mean (nm) | 39.2 | 49.8 | 68.3 | 111.5 | 111.5 |
| Mode (nm) | 30.5 | 43.7 | 58.3 | 504.8 | 504.8 |
| Geo. St. Dev. | 1.6 | 1.67 | 1.86 | 2.18 | 2.18 |
| Total Conc. | 5.13e+04 (#/cm$^3$) | 2.26 (mm/cm$^3$) | 4.10e+08 (nm$^2$/cm$^3$) | 5.85e+09 (nm$^3$/cm$^3$) | 5.85 (μg/m$^3$) |

TABLE 2

| 30 nm SiO2 | Number Particle Size | Diameter Particle Size | Surface Particle Size | Volume Particle Size | Mass Particle Si |
|---|---|---|---|---|---|
| Median (nm) | 62.4 | 85.7 | 116.2 | 156.4 | 156.4 |
| Mean (nm) | 72.9 | 99.1 | 136.5 | 193.2 | 193.2 |
| Geo. Mean (nm) | 62.6 | 84.9 | 115.9 | 161.5 | 161.5 |
| Mode (nm) | 58.3 | 89.8 | 119.7 | 148.6 | 148.6 |
| Geo. St. Dev. | 1.73 | 1.74 | 1.76 | 1.81 | 1.81 |
| Total Conc. | 2.79e+05 (#/cm$^3$) | 20.3 (mm/cm$^3$) | 6.33e+09 (nm$^2$/cm$^3$) | 1.44e+11 (nm$^3$/cm$^3$) | 144.0 (μg/m$^3$) |

Figure 2:
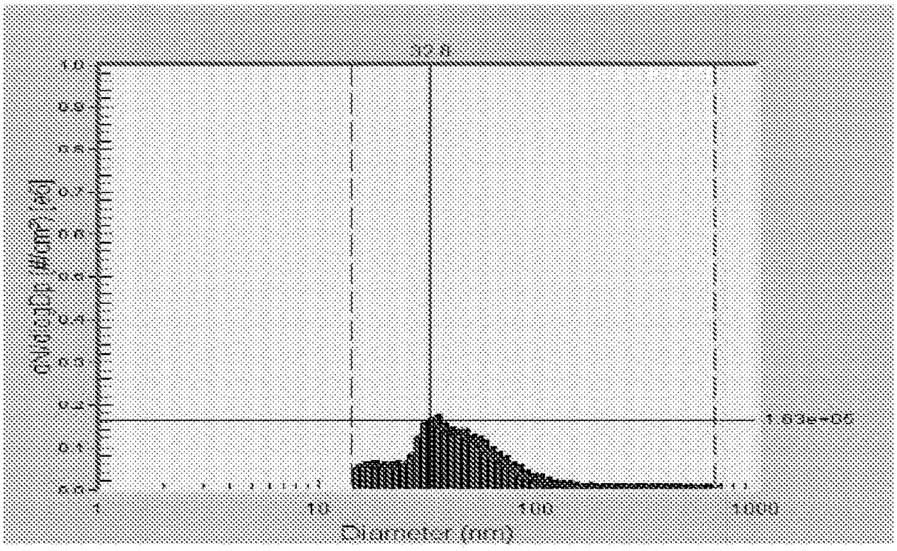
FIG. 2 is a graph of the distribution of diameters of nano-particles sorted by number from the proof of principle experiments shown in Table 1.
Figure 3:
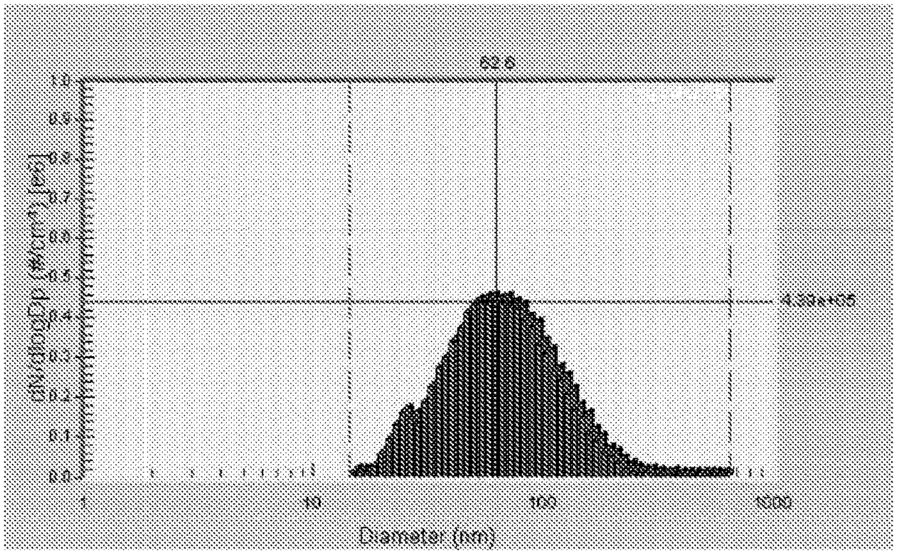
FIG. 3 is a graph of the distribution of diameters of nano-particles sorted by number from the proof of principle experiments shown in Table 2.
Figure 5:
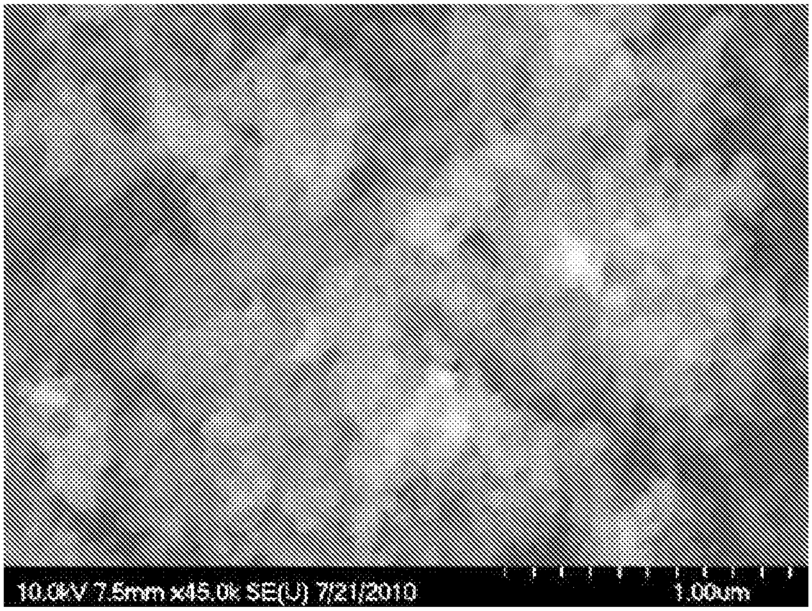
FIG. 5 is an SEM image of the particles from the proof of principle experiments described in FIG. 3 and shown in Table 2.
Figure 6:
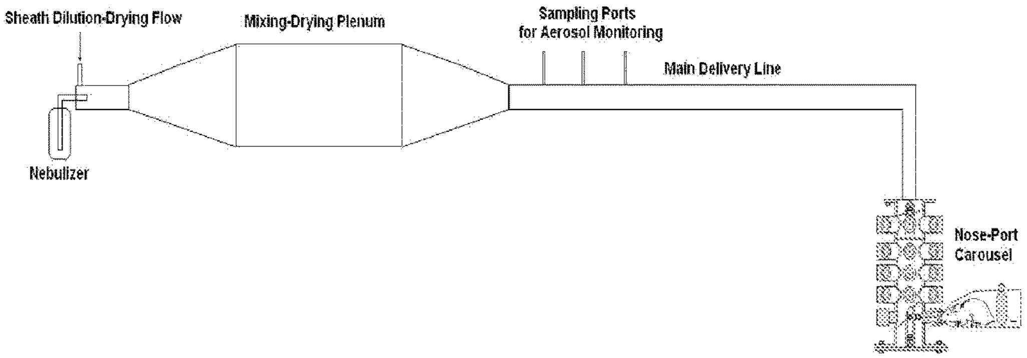
FIG. 6 is a schematic illustration of the inventive apparatus that includes a nose port for exposing an animal subject to a stream of solid nanoparticles entrained in a mixture of helium and air.

Tables 1 and 2 show the proof of principle results for the aerosolization of 30 nm nano-particles of $SiO_2$ using methods and apparatus of the present invention. Corresponding Graphs of the diameter of the nano-particles and the number of particles are shown in FIGS. 2 and 3, where FIG. 2 corresponds with Table 1, and FIG. 3 corresponds with Table 2. An SEM image of the results described in FIG. 3 and shown in Table 2 is shown in FIG. 5.

TABLE 3

| 15 mn Fe3O4 (—COOH) | Number Particle Size | Diameter Particle Size | Surface Particle Size | Volume Particle Size | Mass Particle Size |
|---|---|---|---|---|---|
| Median (nm) | 93.2 | 120.9 | 150.8 | 177.6 | 177.6 |
| Mean (nm) | 104 | 129.7 | 154.5 | 176 | 176 |
| Geo. Mean (nm) | 91.8 | 117 | 142.7 | 166.1 | 166.1 |
| Mode (nm) | 96.5 | 128.6 | 159.6 | 228.8 | 228.8 |
| Geo. St. Dev. | 1.67 | 1.6 | 1.52 | 1.43 | 1.43 |
| Total Conc. | 3.77e+05 (#/cm$^3$) | 39.2 (mm/cm$^3$) | 1.60e+10 (nm$^2$/cm$^3$) | 4.12e+11 (nm$^2$/cm$^3$) | 2.06e+03 (μg/m$^3$) |
| Dilution Factor | 10 | 10 | 10 | 10 | 10 |
| Total Conc. (adjusted to Dil Factor) | 3.77E+006 | 392 | 1.60E+011 | 4.12E+012 | 20600 (μg/m$^3$) |

Figure 4:
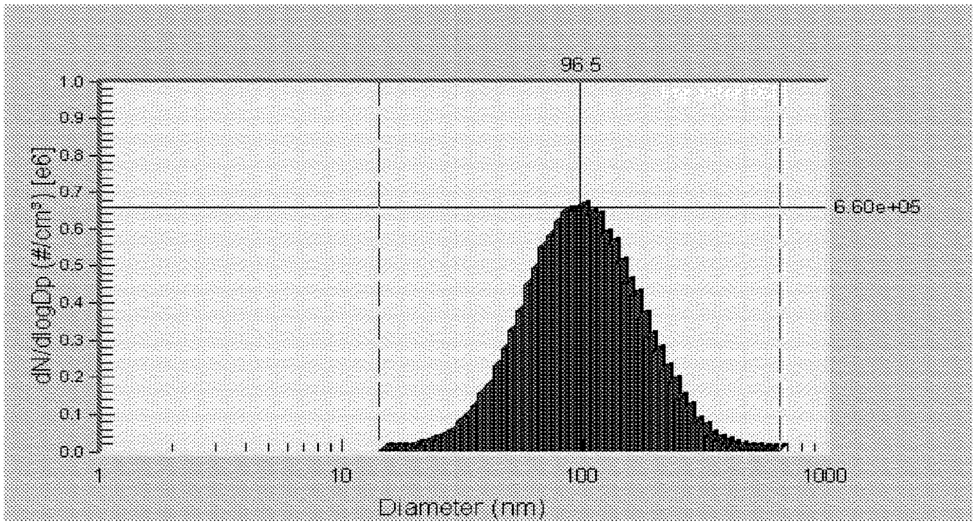
FIG. 4 is a graph of the distribution of diameters of nano-particles sorted by number from the in-vivo inhalation experiments shown in Table 3.

Table 3 shows the results for the aerosolization of nanoparticles of 15 nm $Fe_3O_4$ (—COOH) during preliminary in-vivo inhalation study using the method and apparatus of the present invention. A corresponding graph of the diameter of the nano-particles and the number of particles is shown in FIG. 4.

In another set of experiments, nano-aerosol was generated out of a water suspension that contained superparamagnetic $Fe_3O_4$ (15 nm) nano-particles with surface modification [—COOH and —$N(CH_3)_3$] synthesized using a reverse micelle method. A single-jet Collison type nebulizer followed by the mixing-drying dilution assembly described above was used. The nano-aerosol was delivered to the stainless-steel nose only exposure unit (multiple-tier carousel) and characterized at the nose-ports. The aerosol concentration and size was continuously monitored using Scanning Mobility Particle Sizer (SMPS). Electric Low Pressure Impactor (ELPI) data and Scanning Electron Microscopy (SEM) images were obtained at earlier stages of the system development. Gravimetric filter analysis was performed, and Micro Orifice Uniform Deposition Impactor (MOUDI) data were obtained. Particle size measured by SMPS can be controlled under wide range from ~30 to ~100 nm CMAD at ~1.4-1.8 GSD (and from ~70 to ~300 nm MMAD at ~1.4-1.8 GSD). Spatial uniformity of nano-aerosol distribution across the nose-only exposure unit was confirmed using SMPS measurements taken at the different nose-ports within and between the tiers.

This in-vivo nose-only inhalation study was conducted using super paramagnetic iron oxide (SPIO) nano-particles at aerosol mass concentration ~10 mg/m3 (confirmed by gravimetric analysis) and at SMPS measured CMAD ~90 nm (MMAD ~180 nm). Male BALB-C mice were exposed for 4 hours. Respiratory physiology measurements were conducted to obtain tidal volume, respiration rate, and minute volume. Magnetic Particle Detection (MPD) analysis was performed to assess lung delivery-deposition efficiency, and significant enhancement was found in comparison with similar study (conducted using the same type of particles but larger size). Tissues, urine, and feces were analyzed using MPD to give a detailed picture of particulate deposition and clearance. The results of this study are shown in Table 4, which compares the results with those reported in A R Martin, RB Thompson and W H Finlay, "*MRI Measurement of Regional Lung Deposition in Mice Exposed Nose-Only to Nebulized Superparamagnetic Iron Oxide Nanoparticles*" JOURNAL OF AEROSOL MEDICINE AND PULMONARY DRUG DELIVERY, Volume 21, Number 4, 2008, pp. 335-341. Notably, the present invention showed that the delivery-deposition efficiency: [Total Deposited Mass]/[Total Inhaled Mass] of 1.807% when compared to the 0.039% result calculated from the results reported by Finlay et al. This result is a delivery-deposition efficiency gain (present invention vs Finlay) of 46.50 times.

TABLE 4

| Present Invention | Finlay |
|---|---|
| CMAD nm (GSD) | |
| 93.2 (1.67) | NA |
| MMAD nm (GSD) | |
| 177.6 (1.43) | 5,600 (1.3) |
| Original Mass concentration of iron in suspension (mg/mL) | |
| 5 | 10 |

TABLE 4-continued

| Present Invention | Finlay |
|---|---|
| Dilution Suspension | |
| 5 | 1 |
| Nebulizer Liquid Expense Rate (mL/min) | |
| 0.328 | 0.07 |
| Expense Rate of iron (mg/min) | |
| 0.328 | 0.7 |
| Total Aerosol Flow Rate (L/min) | |
| 32 | 4.7 |
| Aerosol mass concentration (mg/L) or (µg/mL) | |
| 0.01 | 0.15 |
| Aerosol mass concentration based on nebulizer expense rate (mg/m^3) | |
| 10.25 | 148.94 |
| Aerosol mass concentration based on Filter Data (mg/m^3) | |
| 8.69 | NA |
| Aerosol mass concentration based on SMPS Data (mg/m^3) | |
| 20.60 | NA |
| Exposure Duration (min) | |
| 240 | 120 |
| Average minute volume based on respiratory phys data at present invention (mL/min) | |
| 72 | 72 |
| Total iron mass inhaled in lungs based on estimation (µg) | |
| 177.12 | 1286.81 |
| Total iron mass deposited in lungs based on MPD-MRI (µg) | |
| 3.2 | 0.5 |
| Delivery-deposition efficiency: [Total Deposited Mass]/[Total Inhaled Mass] | |
| 1.807% | 0.039% |
| Delivery-deposition efficiency gain (present invention vs Finlay) | |
| 46.50 | |

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

We claim:

1. A method for producing a flow of an aerosol comprising nano-particles comprising the steps of:

providing a Collison nebulizer in communication with a plenum, introducing nano-particles into the Collison nebulizer as a colloidal suspension in water, providing a helium gas flow into the Collison nebulizer, thereby entraining the nano-particles into the helium gas flow, directing the nano-particles entrained in the helium gas flow out an exit of the Collison nebulizer and into the plenum, and providing a flow of dry air through an inlet around the nano-particles entrained in the helium gas flow in the plenum.

2. The method of claim 1 wherein the nano-particles are synthesized in water.

3. The method of claim 1 wherein the plenum is provided as having a reduction in the circumference of the plenum downstream from the inlet, wherein the reduction in the circumference of the plenum is in the direction of flow from the inlet through the plenum, and further including the step of generating a venturi effect at the reduction in the circumference of the plenum, thereby accelerating and mixing the nano-particles entrained in the helium gas flow.

4. The method of claim 1 wherein the plenum is provided as having uniformity screen and flowing the dry air through the uniformity screen.

5. The method of claim 4 wherein the plenum is provided as having a reduction in the circumference downstream from the uniformity screen, and further including the step of generating a venturi effect at the reduction in the circumference of the plenum, thereby accelerating and mixing the nano-particles entrained in the helium gas flow.

6. The method of claim 1 wherein the step of providing the helium gas flow into the Collison nebulizer is conducted at a helium pressure of 94 psi (6.5 bar) or more.

7. The method of claim 1 wherein the nano-particles comprise $SiO_2$.

8. The method of claim 1 wherein the nano-particles comprise metal oxides.

9. The method of claim 8 wherein the metal oxide nano-particles comprise functional groups attached to the surface of the nano-particles.

10. The method of claim 1 wherein the nano-particles entrained in the helium gas an average particle size of 100 nm or less.

11. The method of claim 1 wherein the dry air comprises a uniform axially symmetrical flow around the nano-particles entrained in the helium gas flow in the plenum.

12. A method delivering an aerosol comprising nano particles to an animal's lungs through the animal's nose comprising the steps of claim 1, and further comprising:

passing the nano-particles entrained in a helium-air mixture through the plenum to a nose port, and allowing an animal to breath the nano-particles through the nose port.

13. The method of claim 12 comprising depositing at least 1.5 mass % of the nano-particles entrained in the helium-air mixture in the animal's lungs.

14. The method of claim 1 wherein the nano-particles are provided as $SiO_2$, $Fe_3O_4$, $Fe_3O_4$ with carboxylated surface modification, $Fe_3O_4$ with amine surface modification, and combinations thereof.

15. The method of claim 1 wherein the dry air comprises at least 30 mol % oxygen.

16. A system for producing a flow of highly concentrated nano-particles comprising:

a Collison nebulizer in communication with a plenum, the plenum provided as having a reduction in the circumference of the plenum, a port for introducing a helium gas flow into the Collison nebulizer, a flow of solid nano-particles entrained in the helium gas flow, an inlet for providing flow of dry air around and in contact with the nano-particles entrained in the helium gas flow in the plenum; and wherein the reduction in the circumference of the plenum is downstream of the inlet and in the direction of flow from the inlet through the plenum; and wherein, during operation, the reduction in the circumference of the plenum occurs after contact of the dry air with the nanoparticles.

17. The apparatus of claim 16 further comprising a uniformity screen within the plenum and disposed between the inlet and the reduction in the circumference of the plenum.

* * * * *